US00PP21604P2

(12) United States Plant Patent
Jauchen

(10) Patent No.: US PP21,604 P2
(45) Date of Patent: Jan. 4, 2011

(54) MINIATURE ROSE PLANT NAMED 'PACFIVE'

(50) Latin Name: *Rosa hybrida*
Varietal Denomination: PACfive

(76) Inventor: Daniel Jauchen, 905 S. Patterson Ave., Santa Barbara, CA (US) 93111

( * ) Notice: Subject to any disclaimer, the term of this patent is extended or adjusted under 35 U.S.C. 154(b) by 0 days.

(21) Appl. No.: 12/584,583

(22) Filed: Sep. 9, 2009

(51) Int. Cl.
*A01H 5/00* (2006.01)

(52) U.S. Cl. ..... Plt./122
(58) Field of Classification Search ..... Plt./122
See application file for complete search history.

*Primary Examiner*—Susan B McCormick Ewoldt

(57) ABSTRACT

A new miniature rose plant which has abundant, red colored flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

2 Drawing Sheets

Botanical designation: *Rosa hybrida.*
Variety denomination: 'PACfive'.

BACKGROUND OF THE INVENTION

The present invention constitutes a new and distinct variety of miniature rose plant, which was developed by artificially pollinating an unnamed seedling (not patented) with an unnamed seedling (not patented). The two parents were crossed in the summer of 2006 and the resulting seed was sown in December 2006, in a controlled glasshouse environment. Out of these seedlings one seedling was selected, as the new variety and named 'PACfive'. The new rose may be distinguished from its seed parent, an unnamed seedling, by the following combination of characteristics:

1. FACfive' has medium double flowers, while the unnamed seedling has big single flowers.
2. 'PACfive' has red colored petals, while the unnamed seedling has pink petals.

The new variety may distinguished from its pollen parent, an unnamed seedling created by the same inventor, by the following combination of characteristics:

1. 'PACfive' , has medium double flowers, while the unnamed seedling has big double flowers.
2. PACfive' has red colored petals, while the unnamed seedling has pale orange petals.

BRIEF SUMMARY OF THE INVENTION

Initial asexual reproduction of 'PACfive' by cuttings was first done in Santa Barbara, Calif., USA. This initial and other subsequent propagations conducted in controlled environments have demonstrated that the characteristics of 'PACfive' are true to type and are transmitted one generation to the next. 'PACfive' is a low and compact miniature rose with good vigor.

The objective of the hybridization of this rose variety for commercial greenhouse culture was to create a new and distinct variety with:

1. Uniform and abundant flowers with good keepability;
2. Attractive long lasting foliage and compact growth;
3. Year round flowering under glasshouse conditions;

4. Suitability for production from softwood cuttings in pots;
5. Durable flowers and foliage which make the variety suitable for distribution in the floral industry.

This combination of qualities was not present in previously available commercial cultivars of this type, known to the inventor, and distinguish 'PACfive' from all other varieties of which I am aware.

The seeds from hybridization were planted in a controlled environment and evaluations were conducted on the resulting plants. 'PACfive' was selected by, Daniel Jauchen, in his development program in Santa Barbara, Calif., USA.

BRIEF DESCRIPTIONS OF THE DRAWINGS

The accompanying color illustrations show as true as is reasonably to obtain in color photographs of this type, the typical characteristics of the buds, flowers, leaves, stems of 'PACfive'. Specifically illustrated in the drawings: On sheet 1/2 1: Young shoot. 2: Bud before opening the sepals. 3: Bud at the stage of opening the sepals. 4: Bud at the stage of opening the petals. 5: Flower during course of opening. 6: Open flower-plan view-obverse. 7: Open flower-plan view-reverse. 8: Fully open flower-plan view-obverse. 9: Fully open flower-plan view-reverse. On sheet 2/2 10: Receptacle showing stamens and pistils. 11: Receptacle showing pistils (stamens and sepals removed). 12: Flower petals, detached-inner surface. 13: Flower petals, detached-outer surface. 14: Bare stem exhibiting thorns and flower attachment. 15: Three leaflets upper side. 16: Three leaflets reverse side. 17: Five leaflets upper side. 18: Five leaflets reverse side.

DETAILED BOTANICAL DESCRIPTION OF THE VARIETY

The following is a detailed description of the Miniature Rose: *Rosa hybrida* 'PACfive'.

The following observations, measurements, values and comparisons describe plants grown in glass houses in Santa Barbara, Calif., USA.

The age of the observed plants were 3 months after propagation by cuttings, and produced as flowering pot plants in container of 10 centimeter in diameter. Environmental conditions in the cultivation area for the observed plants, has been temperatures from 64 to 78 degree Farenheit, and 10 to 20 hours day length with assimilation light. Light levels from 600 foot candle to 6000 foot candle. The relative humidity has been ranging from 50 to 85%.

Color references are made using The Royal Horticultural Society (London, England) Colour Chart, 1995, except where common terms of color are used.

For a comparison, the nearest existing rose variety is 'JENwo', a rose variety described and illustrated in U.S. Plant Pat. No. 16,905.

Chart 1 details several physical characteristics of 'PACfive' and 'JENwo'.

CHART 1

| | 'PACfive' | 'JENwo' |
|---|---|---|
| Petal color, Upper surface | Red Group 45A | Red Group 46A |
| Petal color, Reverse surface | Red Group 45B | White Group 46A |
| Petal count | 65-70 | 20 |

*Parents.*—Unnamed seedling ×unnamed seedling.

Classification:

*Botanical: Rosa hybrida.*

*Commercial: Miniature.*

Plant:

*Plant growth.*—Moderately vigorous. Grows compact upright to bushy. When grown as 10 cm pot plant, the average height of the plant itself is 18 cm to 20 cm, and average width is 20 cm. When grown as a 15 cm pot plant, the average height of the plant itself is 22 cm to 27 cm, and average width is 30 cm.

Stem:

*Color.*—Young wood: Green Group 137D. Older wood: Green Group 137B to 137C.

*Thorns.*—Incidence: 2 to 3 per stem. Size: 1 to 3 mm. Form: Deep concave. Color: Greyed-Purple Group 185D.

*Surface.*—Young wood: Smooth. Older wood: Smooth.

Stem diameter.—2 mm to 3 mm.

*Internode length.*—25 mm to 35 mm.

*Numbers of internodes.*—5 to 6.

Plant foliage: Leaves arranged alternately, compound with 3 to 5 leaflets per leaf, generally symmetrical, abundant, and flat in aspect. Stipules at petiole base.

*Quantity of leaves.*—5 to 6 per lateral branch.

*Leaf size.*—Length 30 mm to 60 mm, width 20 mm to 40 mm.

*Petioles.*—Color: Green Group 137B, with intonations of Greyed-Purple Group 184A. Margins: Entire. Length: 6 mm to 15 mm Diameter: about 0.5 mm to 1 mm.

*Stipules.*—Size: Length 1 mm to 3 mm, width 1 mm to 2 mm. Surface: Smooth. Color for upper surface: Green Group 136A, Color for lower surface: Green Group 137D, Margins: Entire. Number if stipules per leaf: two.

*Rachis: Color: Green Group* 137B, with intonations of Greyed-Red Group 181A Margins: Entire. Length: 8 mm to 12 mm. Diameter: 0.5 mm to 1 mm.

*Leaflets.*—Edge: Serrated. Serration: Single. Shape: Ovate with acute apex and obtuse base. Texture: Smooth. Appearance: Dull. Size: length: 10 mm to 25 mm, width: 7 mm to 18 mm. Color: Young foliage: Upper surface: Green Group 137D. Lower surface: Green Group 136D. Color: Mature foliage: Upper surface: Green Group 139A. Lower surface: Green Group 136C. Leaf vein color: Upper surface: Green Group 139A. Reverse surface: Green Group 136D.

Inflorescence:

*Blooming habit.*—Recurrent.

*Number of flowers.*—Generally one bud per flowering stem.

*Peduncle.*—Color: Green Group between 137B and 137D. Texture: Smooth. Length: 20 mm to 25 mm Diameter: 2 mm to 3 mm. Strength: Upright.

*Receptacle.*—Surface: Smooth, glabrous. Shape: Funnel-shaped. Size: Height 5 mm to 6 mm, width 4 mm to 8 mm. Color: Green Group 137B.

*Sepals.*—Quantity: five. Shape: Narrowly ovate w. acute tip. Texture: Leathery. Margin: Foliaceous appendages on three of the five sepals. Appearance: Dull. Color: Upper surface: Green Group between 137A and 137B. Reverse surface: Green Group between 137B and 137C. Size: Length 25 mm to 35 mm, width 3 mm to 5 mm.

*Buds.*—Size: Height 12 mm to 18 mm, diameter 10 mm to 15 mm, Upon opening. Shape: Ovoid. Color: at ¼ opening, Red Group 45A.

*Flower.*—Duration: As a pot plant, flowers last from 21 to 28 days. Fragrance: Slightly parfume. Size: 30mm to 45 mm in diameter. Depth: 20 mm to 25 mm. Form: Shape of flower when viewed from the side: Upon opening: Cupped to ovoid. Open flower: Flat. Color: Petals, upon opening: Upper surface: Outer petals Red Group 45A. Inner petals Red Group between 45A and 45B. Petaleye: White Group 155C Reverse surface: Outer petals Red Group 45B. Inner petals Red Group between 45B and 45C. Petaleye: White Group 155C. Petals after opening: Upper surface: Outer petals Red Group 45A. Inner petals Red Group between 45A and 45B. Petaleye: White Group 155C. Reverse surface: Outer petals Red Group 45B. Inner petals Red Group between 45B and 45C. Petaleye: White Group 155C. General tonality: On open flower: Third day: Red Group 45A. Afterwards: Red Group 46A

*Petals.*—Petal reflex: Outermost petals reflex backwards at opening. Fully open all petals reflex backwards. Texture: Smooth. Petal edge: Entire. Petal count: 55 to 60 on the average per flower. Petal size: Length 10 mm to 22 mm, width 8 mm to 25 mm. Shape: Outer petals: Round - ovate. Inner petals: Ovate. Apex: Rotundate. Base: Obtuse to rotundate.

*Petaloids.*—none.

*Reproductive organs.*—Stamen number: Approximately 20 to 25 on average per flower. Stamens length: 4 mm to 6 mm. Pollen: Color: Greyed-Orange Group 168B. Abundance: Heavy. Anthers: Size: 1 mm to 2 mm Color: Greyed-Orange Group 165C. Shape: Oblong. Filaments: Size: 2 mm to 3 mm. Color: White Group 155C. With intonations of Greyed-Purple Group 186B. Pistils number: Approximately 50 to 55 on average per flower. Stigmas: Location: Protrude more than the anthers. Color: White Group 155A. Styles: Color: White Group 155C, with intonations of Greyed-Purple Group 186D. Length: 5 mm to 6 mm.

Development:

*Vegetation.*—Dense.

*Blooming.*—Abundant.

*Aptitude to bear fruit.*—Poor.

*Resistance to diseases.*—Above average resistance to mildew and Botrytis under normal growing conditions in Santa Barbara, Calif., USA. Hips/seeds has not been observed due to that the plant has never been grown to the stage of seed development, due to the fact, that the variety is developed for use as a flowering pot plant only.

*Winter hardiness & Drought/heat tolerance.*—Due to the fact, that this variety is a potted flowering plant, developed indoor use only, the plant is not tested for winter hardiness or drought/heat tolerance.

The invention claimed is:

1. A new and distinct variety of Rose plant of the miniature class, substantially as herein illustrated and described as a distinct and novel rose variety due to its abundant red flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *

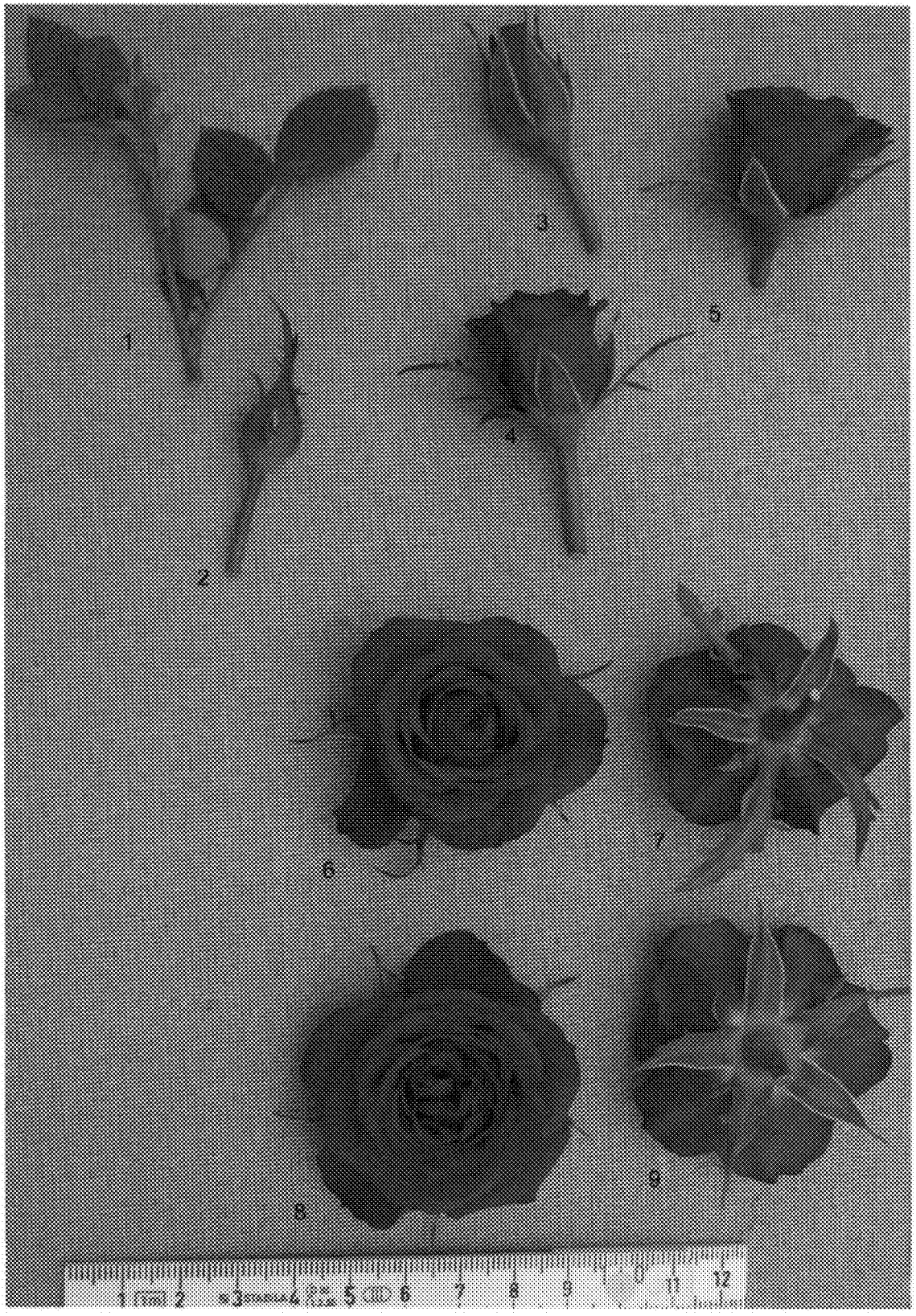
1
2
3
4
5
6
7
8
9

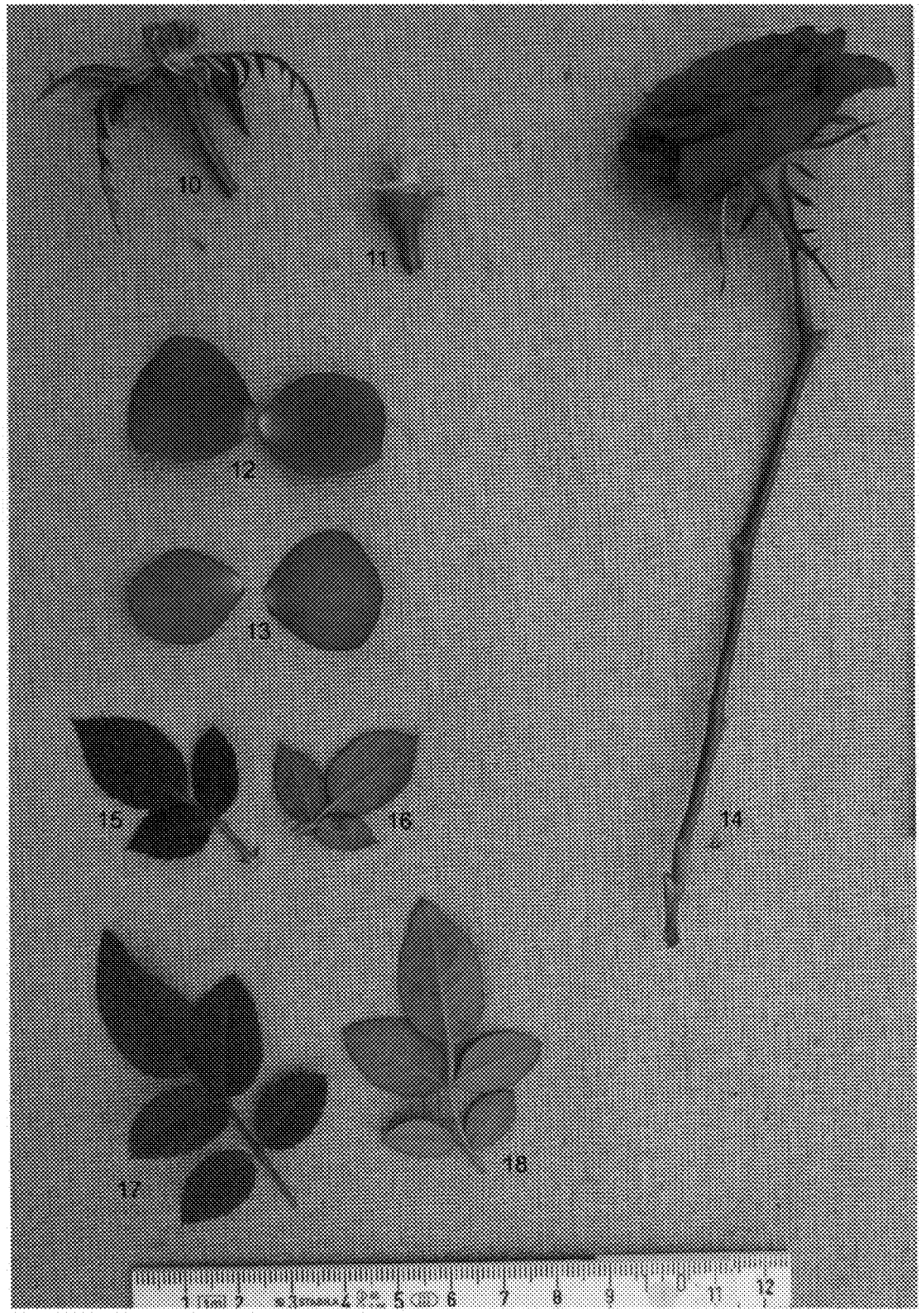
10
11
12
13
14
15
16
17
18